(12) United States Patent
Gavin et al.

(10) Patent No.: US 11,930,781 B2
(45) Date of Patent: Mar. 19, 2024

(54) MILKING SYSTEM WITH DETECTION SYSTEM

(71) Applicant: LELY PATENT N.V., Maassluis (NL)

(72) Inventors: Peter Michael Gavin, Maassluis (NL); Abram Christiaan Knip, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 594 days.

(21) Appl. No.: 17/273,980

(22) PCT Filed: Sep. 19, 2019

(86) PCT No.: PCT/NL2019/050627
§ 371 (c)(1),
(2) Date: Mar. 5, 2021

(87) PCT Pub. No.: WO2020/067886
PCT Pub. Date: Apr. 2, 2020

(65) Prior Publication Data
US 2021/0185972 A1    Jun. 24, 2021

(30) Foreign Application Priority Data
Sep. 24, 2018 (NL) .................................... 2021689

(51) Int. Cl.
*A01J 5/013* (2006.01)
*A01J 5/007* (2006.01)
*G01N 33/04* (2006.01)

(52) U.S. Cl.
CPC .............. *A01J 5/0131* (2013.01); *A01J 5/007* (2013.01); *A01J 5/0135* (2013.01); *G01N 33/04* (2013.01)

(58) Field of Classification Search
CPC ........ A01J 5/0135; A01J 5/0131; A01J 5/045; A01J 5/007
See application file for complete search history.

(56) References Cited

U.S. PATENT DOCUMENTS

| 5,096,828 A | 3/1992 | Ishizaka et al. |
| 2002/0124803 A1* | 9/2002 | Chen ........................ A01K 1/12 119/14.08 |

(Continued)

FOREIGN PATENT DOCUMENTS

| CN | 102933355 A | 2/2013 |
| CN | 103648268 A | 3/2014 |

(Continued)

OTHER PUBLICATIONS

International Search Report, issued in PCT/NL2019/050627, dated Feb. 20, 2020.

(Continued)

*Primary Examiner* — Christopher D Hutchens
(74) *Attorney, Agent, or Firm* — Birch, Stewart, Kolasch & Birch, LLP

(57) ABSTRACT

A milking system includes a milking device, a milk line, and a sampling and analysis device for the milk that includes a control unit, a tape mover to move and unwind a tape wound on a tape reel and with a base material with reagent pads, that detect a substance in the sample, and a dosing device to provide the sample onto a reagent pad, and a sensor to detect radiation from said reagent pad, and to analyse the detected radiation to indicate a presence or concentration of said substance. The reagent pad is facing downward during provision of the sample. In this way, the chance of excess liquid falling from the reagent, and possibly onto a camera, is reduced. Smaller reagent pads may be used, it reduces the chance of supplied liquid spilling over to a neighbouring reagent pad, the measures preventing this spilling may be limited, and it is easier to suck away excess fluid.

20 Claims, 1 Drawing Sheet

(56) References Cited

U.S. PATENT DOCUMENTS

Figure 1:
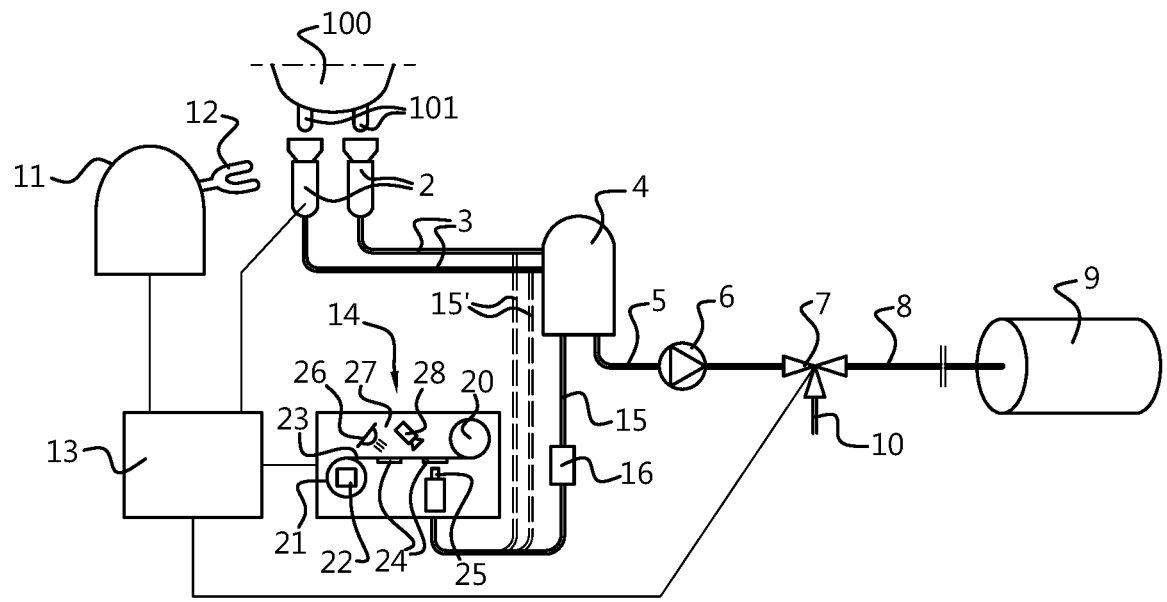

2007/0283893 A1* 12/2007 Schuster ................ A01J 5/007
  119/14.02
2013/0074775 A1  3/2013 Andersson et al.
2014/0174598 A1  6/2014 Hoefelmayr

FOREIGN PATENT DOCUMENTS

| NL | 2008203 C | 8/2013 |
| WO | WO 02/069897 A1 | 9/2002 |
| WO | WO 2004/034063 A2 | 4/2004 |

OTHER PUBLICATIONS

Written Opinion of the International Searching Authority, issued in PCT/NL2019/050627, dated Feb. 20, 2020.

* cited by examiner

MILKING SYSTEM WITH DETECTION SYSTEM

The present invention relates to a milking system, comprising a milking means for milking milk from a dairy animal, a milk line in fluid connection with the milking device, a sampling and analysis device arranged to take a sample of the milk from the milk line and to analyse milk from the sample, wherein the sampling and analysis device comprises a control unit for controlling the sampling and analysis device, a tape mover, arranged to move and unwind, under the control of the control device, a tape wound on a tape reel carrying the tape, said tape comprising a base material with provided thereon a series of reagent pads that are arranged to provide a detectable response in the presence of at least one substance in the sample, a dosing device arranged to provide, under the control of the control unit, a part of the sample onto one of the reagent pads, and an optical sensor device arranged to detect optical radiation from said reagent pad supplied with said part of the sample, and to analyse the detected optical radiation to provide an indication of a presence or concentration of said at least one substance.

Document WO02069697A1 discloses an apparatus for analysing milk samples, thus for use in a milking system, in which apparatus drops of milk are supplied to a tape carrying dry test sticks with reagent. A general desire for such apparatus is that they can be used in milking systems during a long time period. In particular milking robots have the advantage of being able to function without human intervention. It is then desirable that peripheral equipment can also perform unattended. Since it may be necessary, or at least desirable, to test each cow at each milking, the number of tests may be very high during any reasonable testing period. For example, a milking robot serving 60 cows, with on average three milkings per day, may require about 2.500 samples in a two week period. Obviously, in order to reduce the amount of reagent used in these samplings, the reagent pads should preferably be small.

A problem with the known apparatus is that it is difficult to allow for smaller reagent pads while still exerting a good control over the sample drop delivery.

It is therefore an object of the present invention to provide a milking system of the kind mentioned above, with an improved control over the supply of the sample to the reagent. Another object is to enable the use of small reagent pads. Yet another object is to minimise spill of sample liquid, as this may be the cause of undesired pollution of the sampling and analysis environment.

The present invention achieves at least one of these objects by means of a milking system according to claim 1, in particular a milking system, comprising a milking means for milking milk from a dairy animal, a milk line in fluid connection with the milking device, a sampling and analysis device arranged to take a sample of the milk from the milk line and to analyse milk from the sample, wherein the sampling and analysis device comprises a control unit for controlling the sampling and analysis device, a tape mover, arranged to move and unwind, under the control of the control device, a tape wound on a tape reel carrying the tape, said tape comprising a base material with provided thereon a series of reagent pads, that are arranged to provide a detectable response in the presence of at least one substance in the sample, a dosing device arranged to provide, under the control of the control unit, a part of the sample onto one of the reagent pads, and an optical sensor device arranged to detect optical radiation from said reagent pad supplied with said part of the sample, and to analyse the detected optical radiation to provide an indication of a presence or concentration of said at least one substance, wherein during provision of the part of the sample the reagent pad is facing downward and an optical path to the optical sensor device passes upwardly through the base material of the tape.

When the reagent pad, i.e. the active and fluid-receiving part, faces downward, gravity assists in the control of sample liquid supply, in that it does not exert an additional force on the liquid during supplying, but rather a counteracting force. This means that the chance of too much liquid being provided onto the reagent is much reduced. This in turn allows the use of a smaller reagent pad, as well as it reduces the chance of supplied liquid spilling over too a neighbouring reagent pad. Alternatively, just because that risk has been reduced, it is now possible to limit the measures that should prevent this spilling, such as a too great distance between the reagent pads or the like. In addition, in case there would still be provided too much liquid to the reagent pad, it is likely that this will be collected again by the sample supply system, since gravity would pull the liquid back into that direction. Moreover, and not in the last place, it is much easier to suck away excess fluid in the system according to the present invention than in the known systems in which droplets are provided from above. In the latter case it is likely that, when a sample droplet falls, or is sucked, onto a reagent pad, air is sucked into a nozzle or sample supplying line. This prevents any liquid from being sucked back, as the connection between the (contents of the) nozzle or sample supplying line has been broken. This will not, or at the most hardly ever, happen in the present case of supplying the sample from below.

Preferably, the reagent pad faces vertically downward during provision of the part of the sample. Herein, "vertically downward" comprises positions in which a plane through (thus parallel with) the pad makes an angle between zero and 20 degrees with the horizontal, more preferably between zero and 10 degrees. Although somewhat larger angles are not excluded by the invention, gravity assists optimally when the reagent pad is as horizontal as possible.

The optical sensor device may be any sensor device able to detect optical radiation coming from the reagent pad. This may be radiation reflected from the reagent pad, transmitted by the reagent pad (and tape), or even emitted by the reagent pad such as fluorescence radiation. The wavelength of the detected radiation may be in the visual range, but also in the ultraviolet range or in the near-infrared range. The detector may be of any type, such as an optical camera. Since the details of the optical sensor are not relevant for the present invention, and the skilled person has easy access to numerous implementations of these sensors, no further details are deemed necessary to give here.

Particular embodiments of the present invention are described in the dependent claims, as well as, together with their features, advantages and effects, in the now following part of the description.

In particular, the milking system according to the invention is provided with said tape reel with said tape, preferably the tape reel being replaceable.

In embodiments, an optical path to the optical sensor passes upwardly through the base material of the tape during said detecting, and in particular during said supplying said part of the sample. Herein, the optical path to the sensor is the path that is followed by radiation from the reagent pad to the optical sensor. This may be a direct straight line in the simplest case, or a different path if use is made or mirrors, lenses or other optical elements, which, incidentally, may make the set-up more compact. In the present embodiments, the optical path will start upwardly at the reagent pad, and first go through the base material of the tape. This ensures that if a drop of the sample liquid would fall off the reagent pad, it will not fall in the direction of the sensor, but rather away from it, which will reduce the likelihood of such drops affecting measuring reliability and accuracy.

In principle, it is sufficient if the dosing device comprises a nozzle to supply the part of the sample. This may be done in the form of supplying one or more droplets of the sample liquid. If the nozzle is sufficiently close to the reagent pad, the latter will be contacted by the droplet, and will suck it into the reagent pad. This requires the nozzle to be (always) rather close to the reagent pads. In order to be more flexible in the design of the analysis device, in embodiments, the dosing device comprises a displaceable nozzle with a supply line for supplying a portion of the milk sample to the nozzle, the nozzle being arranged for supplying the part of the sample to the reagent pad, wherein the dosing device further comprises a nozzle mover that is arranged to move the displaceable nozzle towards and away from the tape under the control of the control unit. This allows to bring the nozzle as close to the reagent pad as desired, which helps in better controlling liquid supply. Not only is it now possible to use tapes and reagent pads of various thickness, but also liquids of varying viscosity and/or surface tension, or more generally of various droplet forming properties. In addition, allowing control of the nozzle position, by means of the control unit, also allows for correcting differences in tape position, such as caused by sagging and so on. Furthermore, it allows to perform other tasks without a need to move the tape, such as cleaning the nozzle. Moreover, it enables to supply a droplet in a position inbetween the reagent pad and the sensor, which in turn makes it possible to analyse the reagent pad without further having to move it. The latter further reduces the chance of surplus liquid falling off the reagent pad, by shocks or vibrations from moving the tape to a different position.

It may suffice in some embodiments if the sample causes a chemical reaction in the reagent pad that emits optical radiation. In such case, an optical radiation source is not required. In most cases, and in corresponding embodiments, it is advantageous to have an optical radiation source that is controlled by the control unit. This allows a good control over the optical radiation emitted onto the reagent pads, and thus also ensures a good accuracy when determining the presence or concentration of a substance based on optical properties of the reagent pad supplied with the sample. Such optical radiation sources may be one or more LEDs, (halogen) incandescent light bulbs, lasers and so on. These may be readily selected by the skilled person.

In embodiments, the dosing device comprises a pump that is controlled by the control unit and is arranged for pumping liquid through the supply line towards the nozzle. The pump helps in controlling the supply of the liquid, mostly milk, in the form of one or more droplets. Herein, it is advantageous that the pump has to work against the action of gravity, in that control over the drop is better. There is no, or at least a very much reduced, chance that liquid suddenly falls off the nozzle or otherwise onto the reagent pad, in an uncontrolled amount. The pump, which is preferably a metering pump such as a peristaltic pump, can then supply a volume of liquid in an even better controlled fashion. The pump is preferably further arranged for sucking back liquid from the nozzle. This allows liquid to be supplied in a very controlled way, in that for example a liquid drop is supplied such that it makes contact with the reagent pad, and is subsequently sucked back in order to break the contact between the droplet and the reagent pad. This enables further control over the liquid supply, and this may prove advantageous in particular in the case of reagent pad/liquid combinations that show a relatively slow transfer speed and/or capillary action, so that there is a relatively long time for controlling this liquid transfer.

In embodiments, the dosing device comprises an overflow device comprising a wall at least partly surrounding the nozzle, an overflow space being provided between the wall and the nozzle, further comprising a discharge connected or connectable to the overflow space. This allows surplus liquid to be collected in the overflow device. This is not only advantageous for collecting inadvertent surplus liquid. in order to prevent droplets from soiling the apparatus. It further allows deliberate flushing of the nozzle with liquid, even in place, without such risk of soiling the apparatus. The sampling and analysis device may e.g. be arranged to supply a cleaning portion of the sample before supplying the part of the sample proper. To do this, the nozzle is first brought in a position relatively remote from the reagent pad. This prevents accidental transfer of liquid to the reagent pad. Subsequently, the control unit arranges the sampling and analysis device, such as a pump thereof, to supply a first part of the sample, here called a cleaning portion, to the nozzle. This cleaning portion exerts a cleaning action on the nozzle, removing older sample liquid and/or dirt that may have remained or collected there, respectively. This cleaning portion is collected in the overflow device, and carried of via the discharged. After this cleaning action, the now clean nozzle may supply a part (droplet) of the sample for transfer to the reagent pad. If desired, The sampling and analysis device may alternatively or further be arranged to supply a separate cleaning fluid, such as water, optionally with a cleaning agent, to the nozzle. Again, this cleaning fluid may be collected in the overflow device, and drained via the discharge. In all these cases, it is advantageous that the supply of liquid, be it milk or other sample fluid, and/or cleaning fluid is against the direction of gravity, so that an optimum control over the flow of liquid may be exerted, and that cleaning may be performed without any further complications.

In embodiments, the milking system further comprises a dosing control device comprising a flat wall part, and a mover arranged to bring the flat wall part and the nozzle into sealing contact. This allows to fill the nozzle just to its rim, thereby repeatably defining a meniscus as the starting point for "growing a droplet" in a controlled fashion. the flat wall part serves as a lid for the nozzle, against which lid the liquid may be pushed to fill the nozzle completely. Herein, "sealing contact" is meant as "touching contact, without actually preventing fluid from escaping, as that might also include trapping air, which is disadvantageous. Surplus liquid may (thus) escape to the sides. What remains of the liquid forms a well-defined meniscus, which is the reference or starting point for the supply of a droplet of a well-controlled, predefined volume. Herein, a metering pump may serve to add an exactly known amount of liquid to that droplet, or better: to the meniscus, in order to form a droplet.

In embodiments, the wall part comprises a flexible material, in particular an elastic membrane. By means of the flexible material, tolerances in the nozzle surface may be accounted for, such that the "sealing contact" is achieved for substantially every nozzle surface. This also allows excess liquid to escape more easily between nozzle surface and the flat wall part. In addition, because the flat wall part is flexible, the counterforce exerted on the liquid is relatively small, and well-defined. All this further helps in the formation of a well-defined meniscus. Herein, "flexible" means that the flat wall part may undergo a detectable elastic deformation under the influence of the pressure of the liquid from the nozzle. The wall part is preferably an elastic membrane, such as in particular a rubber membrane.

In embodiments, the sampling and analysis device comprises a sealing rim arranged around the flat wall part, the sealing rim and the flat wall part together forming a second space for receiving the nozzle. This ensures that liquid that escapes between the flat wall part and the nozzle, and thus moves more or less to the side, is not ejected into the space of the sampling and analysis device, but may now (also) be collected in the second space, and e.g. drained.

In embodiments, the wall of the overflow device and the sealing rim are in sealing contact when the nozzle is received in the second space, the overflow space and the second space then being in direct fluid connection. This ensures that the draining of the ejected excess liquid may be via the drain of the overflow space.

In embodiments, the discharge has a cross-sectional discharge area that is at least twice as large as a cross-sectional supply area of the supply line. This ensures that the discharge of the collected liquid/excess liquid is substantially always possible with a low pressure/low vacuum, which helps in preventing draining problems, as well as prevents counterpressure on the liquid in the nozzle. Preferably, the discharge area is at least four times as large as said cross-sectional supply area of the supply line. Such a ratio ensures in almost all practical cases a sufficiently large counterpressure, and thus an even better control over the meniscus.

Importantly, many of the above described advantages are not limited to the use of the sampling and analysis device in a milking system. Rather, the ability to better control delivery or supply of a part of a sample to a reagent using gravity in the process may be used in substantially any liquid sampling and analysis system. Therefore, the present invention also provides a sampling and analysis device arranged to receive a sample of a liquid from a sample liquid line, and to analyse liquid from the sample, wherein the sampling and analysis device comprises a control unit for controlling the sampling and analysis device, a tape mover, arranged to move and unwind, under the control of the control device, a tape wound on a tape reel carrying the tape, said tape comprising a base material with provided thereon a series of reagent pads, that are arranged to provide a detectable response in the presence of at least one substance in the sample, a dosing device arranged to provide, under the control of the control unit, a part of the sample onto one of the reagent pads, an optical sensor device arranged to detect optical radiation from said reagent pad supplied with said part of the sample, and to analyse the detected optical radiation to provide an indication of a presence or concentration of said at least one substance, wherein during provision of the part of the sample the reagent pad is facing downward and away from the optical sensor. It is expressly noted that all the features of all dependent claims, as well as of all embodiments described for the milking system according to the invention are also applicable to the sampling and analysis device, with corresponding advantages.

It is furthermore expressly stated here that the advantages for the present invention, both for the milking system and for the sampling and analysis device, also apply to embodiments wherein the tape mover and the tape with the reagent pads have been replaced by a dry stick mover, arranged to move, under the control of the control device, a dry stick, said dry stick comprising a base material with provided thereon one or more reagent pads, that is/are arranged to provide a detectable response in the presence of at least one substance in the sample. Herein, the reagent pad(s) will be facing downward during sample supply. Thus, the invention also relates to a milking system, comprising a milking means for milking milk from a dairy animal, a milk line in fluid connection with the milking device, a sampling and analysis device arranged to take a sample of the milk from the milk line and to analyse milk from the sample, wherein the sampling and analysis device comprises a control unit for controlling the sampling and analysis device, a dry stick mover, arranged to move, under the control of the control device, a dry stick, said dry stick comprising a base material with provided thereon one or more reagent pads, that is/are arranged to provide a detectable response in the presence of at least one substance in the sample, a dosing device arranged to provide, under the control of the control unit, a part of the sample onto one of the reagent pads, an optical sensor device arranged to detect optical radiation from said reagent pad supplied with said part of the sample, and to analyse the detected optical radiation to provide an indication of a presence or concentration of said at least one substance, wherein during provision of the part of the sample the reagent pad is facing downward and away from the optical sensor.

Figure 2:
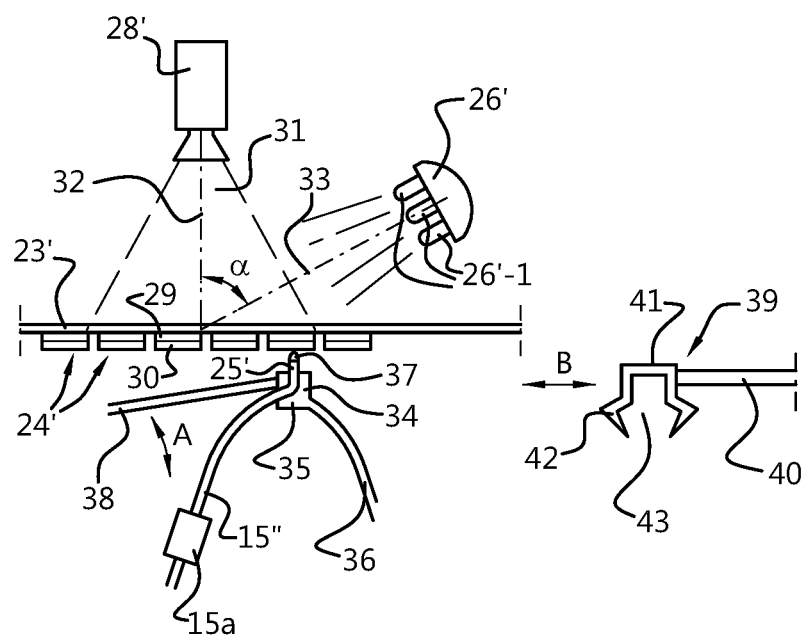

The invention will now be elucidated by way of a number of exemplary embodiments and the drawings, in which FIG. 1 shows a diagrammatic representation of a milking system according to the present invention; and FIG. 2 diagrammatically shows a partly cross-sectional view through a part of an embodiment of the invention.

FIG. 1 shows a diagrammatic representation of a milking system 1 according to the present invention for milking teats 101 of an udder 100 of a dairy animal. The milking system 1 comprises teat cups 2, connected to short milk lines 3, debouching in a milk jar 4, that in turn is connected to a main milk line 5. A milk pump is denoted 6, and a three-way valve with 7 connects to a bulk tank line 8 connected to a bulk milk tank 9, and to a sewer line 10.

A milking robot 11 has a robot arm 12 and a robot control unit 13. A sampling unit is generally denoted 14, and a sampling line 15 with an optional sample valve 16. The sampling unit 14 comprises a supply reel 20 and a collecting reel 21 that is driven by a tape mover 22, for positioning a tape 23 with reagent pads 24. A nozzle device for sample droplets is denoted by 25, a light source 26 emits light 27, and a camera is denoted by 28.

In use of the milking system 1, the robot control unit 13 controls the milking robot 11 with the robot arm 12 to attach the teat cups 2 to the teats 101 of the udder 100 of a dairy animal such as a cow. The milk that is subsequently milked leaves the teat cups 2 under the influence of a vacuum, that is applied by a pump not depicted here, via the short milk lines 3, and is collected in a milk jar 4.

In order to comply with legal requirements, the first milk from each teat must be tested for physical changes, and if desired for other deviant properties. This can be done by means of a separate foremilk test device, or it can be done with the help of the sampling unit 14 as supplied according to the invention. Then use will be made of the alternative sample lines 15'. In case of a negative assessment, the milked milk collected in the milk jar 4 will then be pumped to the sewer line 10 by means of the milk pump 6, via the main milk line 5 and the three way valve 7. All these devices are under the control of the robot control unit 13. Contrarily, if the milk is assessed to be of good quality, it will be pumped to the bulk milk tank 9 via the bulk line 8.

It is also possible that the sampling unit 14 takes a sample from the milk jar 4, in particular a mixed sample from milk that was milked from all teats and during all of the milking. This helps to get a good assessment of all the milk that (if not rejected based on the foremilk assessment or otherwise, such as being antibiotics milk) will be sent to the bulk tank 9, or possible to one of several bulk milk tanks. For example, the milk from different cows could be sent to different bulk tanks, based on their fat content, their protein content or otherwise, as determined by the sampling unit 14. In such embodiments, as the one shown in FIG. 1, the sample line 15 runs from the milk jar 4 to the sampling unit 14, and optionally has a sample valve 16. Note that the latter could also be a part internal to the sampling unit 14.

Most often, however, the sampling unit 14 is used to determine a property of the milk from a cow, either per teat quarter 101 or for the whole udder 100/animal, which property is subsequently used in animal management but not for immediate control of the milk destiny. Examples are the measurement of hormones such as progesterone, that play a role in the reproductive cycle of the animal, or of substances that relate to feeding or metabolic health of the animal. Based on the assessment by the sampling unit 14, the farmer or the control unit 13 may then adapt feeding, call a veterinary for a health check or for insemination, and so on. It is remarked that in robotic milking systems animal identification systems are present, so that animal ID during milking is known. Thereby, any measurement result will be coupled to the corresponding animal file in a database system.

Furthermore, a sampling unit 14 is very generally shown here, in that it contains a supply reel 20 and a collecting reel 21, between which a tape 23 is advanced by means of tape mover means 22, such as a cassette deck motor or stepper motor. The tape 23 carries reagent pads 24 that contain reagent that gives a detectable response in the presence of a defined substance, often the intensity of the response depending on the concentration of the substance brought into the reagent via the sample droplet. Such a sample droplet is delivered via the nozzle 25. A light source 26 then shines light 27 onto the reagent pad 24, and a camera 28 observes the response, if any, in the reagent pad. The light source 26 may be any suitable light source, such as one or more LEDs, and the emitted light 27 may be visible light, UV(A) radiation, (near) infrared, and so on, depending on the used reagent. Of course, the camera 28 should be adapted to detect radiation coming from the reagent pad 24. Often, this is reflected or scattered light, but it could be different radiation, such as fluorescence radiation. In any case, details of such radiation and detection may easily be implemented by the skilled person and do not form the present invention as such.

In the embodiment shown, the sample droplet is supplied to the reagent pad 24 by the nozzle 25 from below. This allows gravity to support the control over the supplying of the sample droplet, instead of interfering with it when the sample droplet would be provided from above or from the side. More details of this will be provided in relation with FIG. 2.

FIG. 2 diagrammatically shows a partly cross-sectional view through a part of an embodiment of the invention. Herein, similar parts are given the same reference numerals, sometimes with a single or double prime ('I').

Here, the tape 23' is provided with a series of reagent pads 24' that have a bottom layer 29 and a top layer 30. The nozzle 25' is connected to the sample line 15" with a sample pump 15a, provides a sample droplet 37, and is provided in, and surrounded by, an overflow cup 34, which has an overflow space 35 with a drain 36 and is connected to a nozzle mover arm 38 that is moveable in the direction of the double arrow A. A rinsing cup 39 is moveable by means of a connected rinsing cup moving arm 40 in the direction of the double arrow B, and comprises a bottom 41 and a bellows 42, and surrounds a rinsing space 43. The camera 28' has a field-of-view 31 with a line of main direction 32. The light source 26' comprises three LEDs 26'-1 and shines in an solid angle with a line of main direction 33, that makes an angle α with line 32.

In use of the system, the droplet 37 is provided from below. This means that gravity in principle pulls back the droplet into the nozzle 25', instead of pulling it out of said nozzle. This helps in controlling the forming and the ejection of the droplet 37. It cannot suddenly drop off from the nozzle, due to some vibration or even mere coincidence. This ensures that the droplet cannot fall from the nozzle onto the camera 28', that images the reagent pads 24'. Even if there would be excess liquid supplied to the reagent pad 24', such liquid would not fall onto the camera, or on an optional window provided between the camera and the tape with the reagent pads. In this way, the camera 28' will always have a clear picture of the reagent pads, even without such a window. In the Figure, the camera is tilted slightly to the left. The tilting of the optical path may also be brought about by means of a mirror or the like.

Having the sample drop supplied from below also allows an improved control over supplying of the droplet in that excess liquid may now easily be sucked off the reagent pad. Again, gravity helps, by preventing breaking off of the droplet from the nozzle, such that in principle there will remain a connection between the droplet, even when contacting the reagent pad, and the nozzle. In case the connection would be broken after all, that is a clear indication that substantially all liquid has been absorbed by the reagent pad, and thus there will neither be a problem with liquid later on falling off unexpectedly. Obviously, the type of sample pump or dosing pump 15a should allow such sucking back, e.g. a peristaltic pump with a reversible pump drive.

In a typical operation of the system, first the nozzle 25' can be rinsed with fluid, to remove residues from previous sampling and/or to bring the nozzle to a desired temperature, by rinsing with correspondingly heated fluid. This may be done by supplying liquid via the sample pump 15a through the sample line 15", and collecting the liquid emerging from the nozzle 25' in the overflow cup 34 by means of gravity. However, it is advantageous if the liquid for rinsing is supplied more vigorously. This can be achieved by moving the nozzle somewhat away from the tape 23' by operating the nozzle mover arm 38 by any suitable means such as pneumatics or an electromotor, and moving the rinsing cup 39 between the nozzle and the tape by operating the rinsing cup moving arm by, again, any suitable means such as an electromotor, followed by inserting the nozzle into the rinsing space 43. In practice this will come down to inserting the nozzle 25' together with the overflow cup 34 into the rinsing space 43. However, if no overflow cup is provided, it is also possible to arrange the rinsing cup with such dimensions that it seals off the nozzle. A drain should then be provided in the rinsing cup 39.

Preferably, when inserted, the nozzle 25' with the overflow cup 34 is sealed by the bellows 42 of the rinsing cup 39. Thereby, the overflow space 35 and the rinsing space 43 form one sealed off space. Now, rinsing fluid may be supplied to the nozzle 25' with vigour, such as with 2 m/s. The liquid will then be ejected from the nozzle but remain within the overflow space/rinsing space 35/43. From there, the fluid will be drained by means of the drain 36. Finally, it will be ensured that the nozzle is completely filled with sample liquid, in particular milk, by pressing the nozzle 15″ against the bottom 41, being a flat part, of the rinsing cup 39 and eject more liquid. The bottom 41 is somewhat elastic, and this ensures that there will be a clearly defined meniscus of sample liquid in the now completely filled, and air bubble-less nozzle. The nozzle arm 38 will then move the nozzle downward, out of the rinsing cup 39, and the rinsing cup moving arm 40 will move the rinsing cup 39 to the side, to clear the way for the nozzle to reach the reagent pads.

Next, a dosing pump, in particular the sample pump 15a, such as a peristaltic pump, may dose a known amount of sample fluid, to form the sample droplet 37 of now known dimensions. This helps in preventing excess fluid that may drop off unexpectedly, and also ensures that it will be known when the droplet 37 will touch the reagent pad 24″. The nozzle mover 38 will then move upward again to bring the droplet 37 to a reagent pad 24', where a reaction and response may be brought about.

This reaction can be observed by the camera 28', that looks straight down through the tape, with a field-of-view 31 with a central line 32. This allows the camera 28' to observe the reaction in the reagent pad 24' from the opposite side with respect to the sample liquid supplied in the droplet 37. This prevents that already coloured reagent material blocks the observation of further response in fresh reagent material, or that not yet absorbed sample liquid blocks the view altogether. This is particularly helpful in double layer reagent pads such as shown in the figure. Sometimes it takes a two-step reaction, such as in the case of flow-through tests. Herein, the present set-up with the double layer may provide an alternative to these flow-through tests or also lateral flow tests. Since these take more time, it is then advantageous when more than one reagent pad 24' is in the field-of-view 31, since the tape and thus each pad 24' is advanced one pad length for every sampling, such as for every milking. Since the latter may be as short as five minutes, it is advantageous to allow more pads in the view of the camera 28' to allow more time for observing the response. It is remarked that even with single layer reagent pads 24', having more pads in view of the camera is useful, since then the concentration of the reagent in the pad 24' may be less than would be needed if the response would have to be assessed in those five minutes.

It is remarked that the camera 28' need not itself be positioned (directly or not) above the tape 23', as long as the optical path (the "view") of the camera 28' is on the other side of the tape 23' as where the reagent pads 24' are. In other words, the camera should look through the tape. The physical position of the camera 28' may be changed e.g. by using mirrors or the like. These may e.g. be used to fold up the optical path, and make the analyser device more compact.

The light source 26' used in the present embodiment comprises three LEDs 26'-1. These can be white light LEDs that together shine a homogeneous but bright light, in a main direction 33 that makes a sharp angle α with the line 32 of the camera's field-of-view, in order to prevent blurring or glaring of the camera image. The light source may also comprise other types, such as a combination of red, green and blue LEDs, halogen incandescent and so on. The light emitted may be visible light, near infrared, ultraviolet (UVA) or the like. The tape 23' should of course be transparent for the light used.

The above described embodiments only serve to help explain the invention without limiting this in any way. The scope of the invention is rather determined by the appended claims.

The invention claimed is:

1. A milking system, comprising a milking device for milking milk from a dairy animal, a milk line in fluid connection with the milking device, and a sampling and analysis device arranged to take a sample of the milk from the milk line and to analyse milk from the sample,
    wherein the sampling and analysis device comprises:
        a control unit for controlling the sampling and analysis device;
        a tape mover, arranged to move and unwind, under the control of the control device, a tape wound on a tape reel carrying the tape, said tape comprising a base material with provided thereon a series of reagent pads, that are arranged to provide a detectable response in the presence of at least one substance in the sample;
        a dosing device arranged to provide, under the control of the control unit, a part of the sample onto one of the reagent pads; and
        an optical sensor device arranged to detect optical radiation from said reagent pad supplied with said part of the sample, and to analyse the detected optical radiation to provide an indication of a presence or concentration of said at least one substance,
    wherein during provision of the part of the sample the reagent pad is facing downward.

2. The milking system according to claim 1, wherein during said detecting, an optical path to the optical sensor passes upwardly through the base material of the tape.

3. The milking system according to claim 2, wherein the dosing device comprises a displaceable nozzle with a supply line for supplying a portion of the milk sample to the nozzle, the nozzle being arranged for supplying the part of the sample to the reagent pad, wherein the dosing device further comprises a nozzle mover arranged to move the displaceable nozzle towards and away from the tape under the control of the control unit.

4. The milking system according to claim 2, wherein the dosing device comprises an overflow device comprising a wall at least partly surrounding the nozzle, an overflow space being provided between the wall and the nozzle, further comprising a discharge connected or connectable to the overflow space.

5. The milking system according to claim 2, further comprising a dosing control device comprising a flat wall part, and a mover arranged to bring the flat wall part and the nozzle into sealing contact.

6. The milking system according to claim 1, wherein the dosing device comprises a displaceable nozzle with a supply line for supplying a portion of the milk sample to the nozzle, the nozzle being arranged for supplying the part of the sample to the reagent pad, wherein the dosing device further comprises a nozzle mover arranged to move the displaceable nozzle towards and away from the tape under the control of the control unit.

7. The milking system according to claim 6, wherein the dosing device comprises a pump controlled by the control unit and arranged for pumping liquid through the supply line towards the nozzle.

8. The milking system according to claim 7, wherein the dosing device comprises an overflow device comprising a wall at least partly surrounding the nozzle, an overflow space being provided between the wall and the nozzle, further comprising a discharge connected or connectable to the overflow space.

9. The milking system according to claim 6, wherein the dosing device comprises a pump controlled by the control unit and arranged for pumping liquid through the supply line towards the nozzle, and is further arranged for sucking back liquid from the nozzle.

10. The milking system according to claim 6, wherein the dosing device comprises an overflow device comprising a wall at least partly surrounding the nozzle, an overflow space being provided between the wall and the nozzle, further comprising a discharge connected or connectable to the overflow space.

11. The milking system according to claim 6, further comprising a dosing control device comprising a flat wall part, and a mover arranged to bring the flat wall part and the nozzle into sealing contact.

12. The milking system according to claim 1, wherein the dosing device comprises an overflow device comprising a wall at least partly surrounding the nozzle, an overflow space being provided between the wall and the nozzle, further comprising a discharge connected or connectable to the overflow space.

13. The milking system according to claim 12, wherein, when the nozzle is received in the second space, the wall of the overflow device and the sealing rim are in sealing contact, the overflow space and the second space being in direct fluid connection.

14. The milking system according to claim 13, wherein the discharge has a cross-sectional discharge area that is at least twice as large as a cross-sectional supply area of the supply line.

15. The milking system according to claim 1, further comprising a dosing control device comprising a flat wall part, and a mover arranged to bring the flat wall part and the nozzle into sealing contact.

16. The milking system according to claim 15, wherein the wall part comprises a flexible material.

17. The milking system according to claim 15, comprising a sealing rim arranged around the flat wall part, the sealing rim and the flat wall part together forming a second space for receiving the nozzle.

18. The milking system according to claim 15, wherein the wall part comprises an elastic membrane.

19. The milking system according to claim 1, wherein during provision of the part of the sample, the reagent pad is facing vertically downward.

20. The milking system according to claim 1, wherein during said supplying said part of the sample, an optical path to the optical sensor passes upwardly through the base material of the tape.

* * * * *